(12) United States Patent
Visco et al.

(10) Patent No.: US 8,380,310 B2
(45) Date of Patent: Feb. 19, 2013

(54) IMPLANTABLE ELECTRODE ASSEMBLY, IMPLANTABLE ELECTROCHEMICAL POWER CELLS AND IMPLANTABLE MEDICAL DEVICE ASSEMBLIES

(75) Inventors: Steven J. Visco, Berkeley, CA (US); Yevgeniy S. Nimon, Danville, CA (US); Bruce Katz, Orinda, CA (US)

(73) Assignee: PolyPlus Battery Company, Berkeley, CA (US)

( * ) Notice: Subject to any disclaimer, the term of this patent is extended or adjusted under 35 U.S.C. 154(b) by 194 days.

(21) Appl. No.: 12/862,154

(22) Filed: Aug. 24, 2010

(65) Prior Publication Data

US 2011/0054561 A1 Mar. 3, 2011

Related U.S. Application Data

(60) Provisional application No. 61/236,818, filed on Aug. 25, 2009, provisional application No. 61/351,787, filed on Jun. 4, 2010.

(51) Int. Cl.
*A61N 1/378* (2006.01)
*H01M 8/16* (2006.01)

(52) U.S. Cl. ............................ 607/35; 607/36
(58) Field of Classification Search ............. 607/35–36; 429/213, 249, 513, 523
See application file for complete search history.

(56) References Cited

U.S. PATENT DOCUMENTS

| | | | |
|---|---|---|---|
| 3,897,267 A | 7/1975 | Tseung et al. | |
| 3,941,135 A | 3/1976 | Von Sturm et al. | |
| 4,294,891 A | 10/1981 | Yao et al. | |
| 5,314,765 A | 5/1994 | Bates | |
| 6,025,094 A | 2/2000 | Chu et al. | |
| 6,096,447 A | 8/2000 | Gan et al. | |
| 7,282,295 B2 | 10/2007 | Visco et al. | |
| 7,282,296 B2 | 10/2007 | Visco et al. | |
| 7,282,302 B2 | 10/2007 | Visco et al. | |
| 7,645,543 B2 | 1/2010 | Visco et al. | |
| 7,666,233 B2 | 2/2010 | Visco et al. | |
| 7,829,212 B2 | 11/2010 | Visco et al. | |
| 2008/0057387 A1 | 3/2008 | Visco et al. | |
| 2009/0005824 A1 | 1/2009 | Visco et al. | |
| 2009/0069740 A1 | 3/2009 | Visco et al. | |
| 2010/0104934 A1 | 4/2010 | Visco et al. | |
| 2011/0014522 A1 | 1/2011 | Visco et al. | |

FOREIGN PATENT DOCUMENTS

WO    2009-050647    4/2009

OTHER PUBLICATIONS

WO patent application No. PCT/US2010/046504, International Search Report and Written Opinion mailed Apr. 29, 2011.
U.S. Appl. No. 11/823,847, Ionically conductive composites for protection of active metal anodes, Visco et al., filed Jun. 27, 2007.

*Primary Examiner* — Rex R Holmes
(74) *Attorney, Agent, or Firm* — Weaver Austin Villeneuve & Sampson LLP

(57) ABSTRACT

Electrochemical power cells having an open-cell architecture for electrically powering an implantable medical device system include a first and a second electrode assembly, wherein at least one is a biocompatible hermetically sealed anode assembly (e.g., that of a lithium anode assembly). The power cell can be a biological lithium semi-fuel cell in which a bodily constituent partakes in the cell discharge reaction at the cathode as an active reagent. The active cathode reagent can be oxygen supplied from the body. In a particularly suitable application, the biological lithium semi-fuel cell provides electrical power to a cardiac pacemaker device, such as for a novel cardiac pacemaker system.

32 Claims, 8 Drawing Sheets

IMPLANTABLE ELECTRODE ASSEMBLY, IMPLANTABLE ELECTROCHEMICAL POWER CELLS AND IMPLANTABLE MEDICAL DEVICE ASSEMBLIES

CROSS-REFERENCE TO RELATED APPLICATIONS

This application claims priority to U.S. Provisional Patent Application No. 61/236,818 filed Aug. 25, 2009, titled IMPLANTABLE ELECTRODE ASSEMBLY, IMPLANTABLE ELECTROCHEMICAL POWER CELLS AND IMPLANTABLE MEDICAL DEVICE SYSTEMS; and U.S. Provisional Patent Application No. 61/351,787 filed Jun. 4, 2010, titled IMPLANTABLE ELECTRODE ASSEMBLY, IMPLANTABLE ELECTROCHEMICAL POWER CELL AND IMPLANTABLE MEDICAL DEVICE SYSTEM. Each of these prior applications is incorporated herein by reference in its entirety and for all purposes.

FIELD OF THE INVENTION

The present invention relates generally to the field of implantable devices, and in particular to devices implanted in a mammalian subject. In one aspect, the invention relates to an implantable electrochemical power cell device for the purpose of providing electrical power to an implantable medical device (IMD). In accordance with this aspect of the invention, the power cell, having what is termed herein an open architecture, includes a hermetically sealed anode assembly and a cathode assembly both of which, when in operation, contact and electrically interface with bodily fluid of the mammalian subject in which they are implanted, and bodily fluid serves as the electrolytic medium between the two assemblies. In one particular embodiment the inventive power cell device is an implantable biological lithium semi-fuel cell, wherein the anode assembly is based on electroactive lithium disposed in an hermetic housing having a lithium ion conductive wall member that electrically interfaces with bodily fluid whence the anode assembly is implanted, and further wherein the electroactive species of the cathode assembly are a constituent of, and supplied by, bodily fluid, e.g., dissolved oxygen that is electro-reduced at the surface of an electron transfer medium during cell discharge. In another aspect the invention relates to an implantable device system having a novel configuration which includes an open architecture implantable power cell electrically coupled to, e.g., an implantable medical device; for instance, the system a novel implantable cardiac pacemaker.

BACKGROUND OF THE INVENTION

Implantable medical devices (IMDs) are designed to work inside a human (or mammal), and are generally used for diagnosing, monitoring and treating diseases and disabilities. When requiring electrical power to operate, these devices are sometimes referred to as active. Today, as we continue to learn more about disease, new and increasingly sophisticated active IMDs are being developed, and our ability to meet the power and energy demands of these devices is becoming increasingly challenging.

Use of and demand for active IMDs is growing at an astounding rate. At the time of this writing applications abound: including, cardiac pacing; defibrillation; pain management; bone growth/repair; and treatment of a variety of maladies including movement and psychological disorders (including Parkinson's disease and epilepsy), scoliosis, hearing/deafness, vision/blindness, incontinence, gastroparesis, sexual dysfunction, cancer, and obesity; and the monitoring of diseases, generally via implantable sensors or detectors (e.g., monitoring cancer and diabetes); and fluid delivery of medicaments. It is clear just from this listing that the breadth of new implantable medical device applications will continue to expand well into the future.

The batteries that provide power to active IMDs are most often determinant of its service life. Indeed, it can be argued that the viability of a power hungry IMD, or that for which long service life is paramount, is linked to advances in battery technology, and in particular to that of lithium batteries, which, today, are the main energy sources in virtually every active IMD. For instance, the service life of the Li/I battery, the established power source of cardiac pacers for the last 30 years, is presently limiting pacemaker performance now that patient life expectancy is beyond 10 years from the date of implant.

The critical link between the success of an IMD and the battery that energizes it is no better exemplified than in the evolution of the cardiac pacemaker, still today the most commonly implanted active IMD Cardiac pacers, which deliver electrical pulses to a patient's heart so that it will beat at a desired rate, were first implanted successfully in the 1960s when they were powered by an implanted zinc/mercuric oxide battery, considered, at that time, to be the industry standard. However, those early pacemakers all suffered from leaks and short service life, the battery lasting, at best, about 2 years, and more typically less than that. Over time major breakthroughs have led to the development of the present day pacemaker. These include: i) hermetic casings and sealing technology, which have enabled significant improvements in patient compliance and device reliability; ii) low impedance electrodes and low power IC circuits, which in turn have led to such dramatic reductions in power requirements that the modern pacemaker is, today, a low power device; iii) the advent of microprocessors and the use of telemetry has enabled smart implantable devices communicable to an external operator; and iv) the innovation of the Li/I battery by Wilson Greatbach provided a dramatic increase in device longevity and reliability, and fostered along with it the era of the modern day pacemaker. When first introduced in about 1972 the Li/I battery provided key advantages over the state of the art, including: enhanced longevity, reliability and end of life predictable, all of which were critical to the eventual long term success of the pacer itself.

Presently more than 300,000 pacemakers are implanted in the United States annually and over 3 million are currently implanted in humans worldwide. Most, if not all, are powered by Li/I batteries. However, with increasing functionality and improvements in the safety of surgical implantations as well as longer patient life expectancy, pacemaker device longevity issues are back at the forefront, and along with that, there is again a need, if not a demand, for a longer lasting implantable power/energy source.

Indeed, the top reason for surgical removal of an active IMD is the need to replace the power source. Change out (i.e., replacing) of an implanted battery, or an entire IMD, can be exceptionally problematic, and is always associated with the inherent risk of infection. Patient preference, not unexpectedly, is almost always to remove that risk. Studies have shown that there is a nearly 7% chance of infection when an IMD is changed out, and this brings with it the possibility of mortality or complications thereafter.

Today there is a mismatch between patient longevity and active IMD service life. The present invention addresses this mismatch at the power/energy source level.

SUMMARY OF THE INVENTION

In one aspect the present invention provides an implantable electrochemical power cell device for providing electrical power to an implantable device, typically an implantable medical device (IMD), such as an electrical stimulator. In various embodiments the power cell device enhances IMD service lifetime, thereby mitigating the need for, or otherwise lessening the frequency of, battery change out and the associated surgical risks that go along with that. In another aspect the invention provides an implantable device system, e.g., a cardiac pacemaker system, energized by a power cell novelly configured to a pacemaker main module (or more generally to an active device component of the system), the power cell having an open architecture wherein a first and a second electrode assembly, each not disclosed in a common hermetic housing, are electronically coupled, preferably detachably, to the main module (device component). In one embodiment the IMD system (e.g., cardiac pacemaker system) has a dual functionality, a primary function, which may be to electrically stimulate the heart of a patient, and a secondary function which is to deliver active metal ions (e.g., lithium ions) to the patient for nutritional or otherwise therapeutic benefit.

In accordance with the instant invention, the implantable electrochemical power cell device has what is termed herein an open architecture, the cell comprising a hermetic anode assembly and a cathode assembly, each of which, when implantably positioned in a mammalian subject, contacts and electrically interfaces with bodily fluid of the mammal in which the cell is implanted and bodily fluid of the mammal serves as the electrolytic medium between the two assemblies. And, moreover, by virtue of the open architecture, the anode assembly and the cathode assembly are not disposed in a common hermetic enclosure.

By use of the term "electrically interfaces" or "electrical interface" when referring to an interface between the electrode assembly and bodily fluid, it is meant that at that interface at least one of electrons or ions are transferred from the electrode assembly into bodily fluid when the cell is actively discharging i.e., when the cell is providing electrical power to the IMD; or vice versa, from bodily fluid into the electrode assembly on charge, if the cell a secondary. Moreover, as used herein the term bodily fluid refers to internal bodily fluid of the subject in which the power cell is implanted, and is intended to include bodily fluid of or within tissue.

In various embodiments the power cell of the instant invention is a biological lithium semi-fuel cell having a hermetically sealed lithium anode assembly and a bio-cathode assembly so named because it makes use of a constituent of the body, typically a constituent of bodily fluid, as the electroactive species, which, when the cell discharges, is electroreduced at the surface of an electron transfer medium of the cathode. For example, oxygen dissolved in bodily fluid is a preferred constituent because of its highly positive electrode potential, which when utilized in conjunction with a lithium anode assembly yields a power cell with an exceptionally high working voltage, typically greater than the electrochemical stability window of the bodily fluid contacting the anode or cathode assembly or that which serves as the electrolytic medium between the assemblies.

Generally, the power cell has a first and a second electrode assembly.

For instance, the first assembly may be a hermetically sealed anode assembly containing an electroactive component material of an active metal, e.g., lithium metal or a lithium alloy or a lithium intercalation material, which, chemically incompatible in contact with bodily fluid, is disposed in the interior of a bodily fluid and, preferably, air impermeable housing. The housing, to allow egress of lithium ions during discharge, has at least one lithium ion conductive wall member, which is a solid bodily fluid impermeable medium through which active metal ions of the anode (e.g., lithium ions) electrically migrate across during discharge. For the reason that the wall member serves an active electrochemical function, it providing a medium for active metal migration out of the assembly under an electric field during discharge, it is generally referred to herein as an active wall member.

The active wall member may be described as having an exterior surface facing the external environment about the housing and an interior surface facing inside the housing. During implantation the anode assembly is positioned in a body cavity to ensure that the exterior surface of the active wall member makes sufficient contact with bodily fluid to establish a suitable electrical interface for the flow of active metal ions, out of the assembly, during discharge. Functional, the active wall member has a number of requisite properties, including that it is conductive to ions of the active metal (e.g., lithium ions); impermeable to bodily fluids, and preferably ambient air, in contact with its exterior surface; and its exterior surface is substantially biocompatible, which is to mean that whence implanted the surface is biocompatible with bodily components that it contacts or interacts with for a substantial period of time, and preferably at least that period of time corresponding to the service life of the anode assembly, and more preferably beyond the lifespan of the subject in which it dwells.

Taking advantage of the biocompatibility of titanium, phosphate and oxide based compounds, preferred materials for defining the exterior surface composition of the active wall member include lithium ion conducting titanium compounds, metal phosphates and metal oxides. For instance, in various embodiments the exterior surface composition and/or the bulk composition of the active wall member is a lithium titanium phosphate compound, of the $LiTi_2(PO_4)_3$ type, or a derivative thereof, such as $LiAl_{0.3}Ti_{1.7}(PO_4)_3$ and the like.

In various embodiments, the active wall member in cooperation with at least one or more other inactive wall members, which is to mean a wall member that does not electrically interface with bodily fluids, are conjoined to form the hermetic anode housing in which the electroactive material is disposed. For instance, the inactive wall member may be a unitary structure in the form of a receptacle having a biocompatible exterior surface and an open end, which, when forming the anode assembly, may be closed off by sealing the active wall member around the periphery of the open end, e.g., the receptacle a titanium capsule. The open end of the receptacle may also be useful for receiving, there through the electroactive material during fabrication of the assembly.

To allow egress of active metal ions (e.g., lithium ions) out of the anode assembly during discharge, the active wall member interior surface must be in active metal ion communication with the electro-active component material, which when electro-reduced during cell discharge emits or otherwise releases lithium ions to maintain a state of charge neutrality. The ionic communication may be established via direct contact between the electroactive component material and the active wall member, where both are sufficiently chemically compatible with each other to maintain a low impedance interface over the lifetime of the assembly. Alternatively, to improve interfacial properties or otherwise device performance, one or more active metal ion conductive interlayers may be interposed between, and in contact with, the interior active wall member surface and the electroactive component material. And when chemical incompatibilities are of a concern, the interlayer(s) may be configured to prevent the interior wall member surface from contacting the electroactive component material. The interlayer may take on a number of forms or phases, including it comprising a liquid, gel or solid (e.g., inorganic) active metal ion conducting material, or some combination thereof, and other materials may be used as well or in addition to, such as, but not limited to, porous or semi-permeable membranes, which may be used to retain a liquid or gel interlayer electrolyte between the active wall member and the electroactive material.

When the first assembly is an anode assembly, the second is therefore a cathode assembly, e.g., a bio-cathode assembly that makes use of a bodily fluid constituent as an electroactive species that is electro-reduced on the surface of an electron transfer medium, which is that component of the cathode assembly that functions to electrically interface with bodily fluid. The electron transfer medium may take any suitable size, shape or form, generally it is an electronic conductor, e.g., a metal foil, sheet or mesh of, e.g., platinum or titanium metal or an alloy thereof, or other electronic conductor having a surface on which the species (e.g., dissolved oxygen molecules) can be electro-reduced, such as a carbon matrix material, non-catalyzed or catalyzed, and with sufficient surface area to support the electrical current passing through the cell.

To enhance the acceptability of the cathode implanted, the edges, corners and/or backside of the electron transfer medium may be embedded or otherwise covered in a biocompatible sheath; for instance, the sheath having smooth contours to mitigate edge and corner effects that are undesirable for an implantable component and especially problematic for one that interacts with the body electrochemically.

The anode assembly housing or the sheath in which the electron transfer medium is embedded may further comprise an electrical feedthrough connector preferably configured for electrical coupling to the implantable medical device; for instance, the power cell having an electrical power lead with a proximal end configured to mate with a feedthrough connector on the assembly (cathode and/or anode) and a distal end mating with, e.g., the IMD.

In another aspect the invention provides an implantable device system generally used to monitor and/or deliver a therapy to a mammalian subject, and in particular to a human subject, such as a cardiac pacemaker system. In various embodiments the system is novelly configured with a power cell having an open architecture where a first and second electrode assembly are independently electrically coupled to the IMD, thus allowing for one or the other of the electrode assemblies to be implanted or changed out independent of the other assembly and/or of the IMD.

In certain embodiments, such as in the case where the anode is based on lithium and the cathode that of oxygen in bodily fluid, the large electrochemical potential of that couple in conjunction with the open architecture of the cell may be used to advantage in allowing for remote positioning of the anode assembly relative to the cathode assembly. This advantage is important when it is desired to locate the anode assembly in a particular body cavity (a first body cavity) and the cathode assembly in a second body cavity or within the first body cavity but at a relatively large distance removed from the anode assembly or when the relative position of each assembly causes the electric field lines between the anode and cathode assembly to take on a curvature, the active wall member of the anode not in face to face relation with the cathode (e.g., where the active wall member and the active surface of the electron transfer medium are disposed in an opposing or a side-by-side relation or some combination thereof such as something other than a face-to-face relation).

In one embodiment the cardiac pacemaker of the instant invention is a dual system device having a primary function which is to provide electrical stimulation to the heart and a secondary function of delivering active metal ions for nutritional or otherwise beneficial purpose, e.g., medicinal use. For instance, dual functionality may be particularly advantageous for the elderly, where lithium deficiency in the diet is common and has been associated with various maladies, including geriatric disorders such as alzheimers and dementia. The amount of lithium delivered to the subject may be directly proportional to the current passing from the power cell to the pulse generator, or where additional lithium is deemed beneficial, the IMD system may be operated to deliver lithium at a rate greater than or at a time other than that which is required by the device component, such as that for stimulating an electrical impulse to the heart or otherwise for powering the pacemaker, including charging an internal battery or capacitor component of the main module for instance.

The invention also provides methods for providing electrical power to an implantable medical device. On account of the power cell open architecture, these methods include the capability of implanting, or removing from the body, one or the other of the anode and cathode assembly sequentially as opposed to simultaneously, since in various embodiments each is physically unconstrained by the other. By the same expedient, various embodiments of the power cell also allow for re-fueling via replacement of the anode assembly without necessitating the need to change out the cathode assembly, or vice-versa in the case where the cathode assembly requires change out but the anode assembly does not.

DETAILED DESCRIPTION OF SPECIFIC EMBODIMENTS

Reference will now be made in detail to specific embodiments of the invention. Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention. In the following description, numerous specific details are set forth in order to provide a thorough understanding of the present invention. The present invention may be practiced without some or all of these specific details. In other instances, well known process operations have not been described in detail so as to not unnecessarily obscure the present invention.

To better understand and appreciate the advantages offered by the present invention, it is first broadly described in the context of a generic implantable medical device system and in a specific embodiment to that of an electrical stimulator, and thereafter, the invention (including that of an IMD system, implantable power cell and hermetic anode assembly) is further described in more detail within the context of a particular inventive embodiment, namely that of an implantable cardiac pacemaker electrically powered by a biological lithium semi-fuel cell having a hermetically sealed lithium anode assembly and a bio-cathode, especially an oxygen bio-cathode assembly.

Implantable Medical Device System

Figure 1:
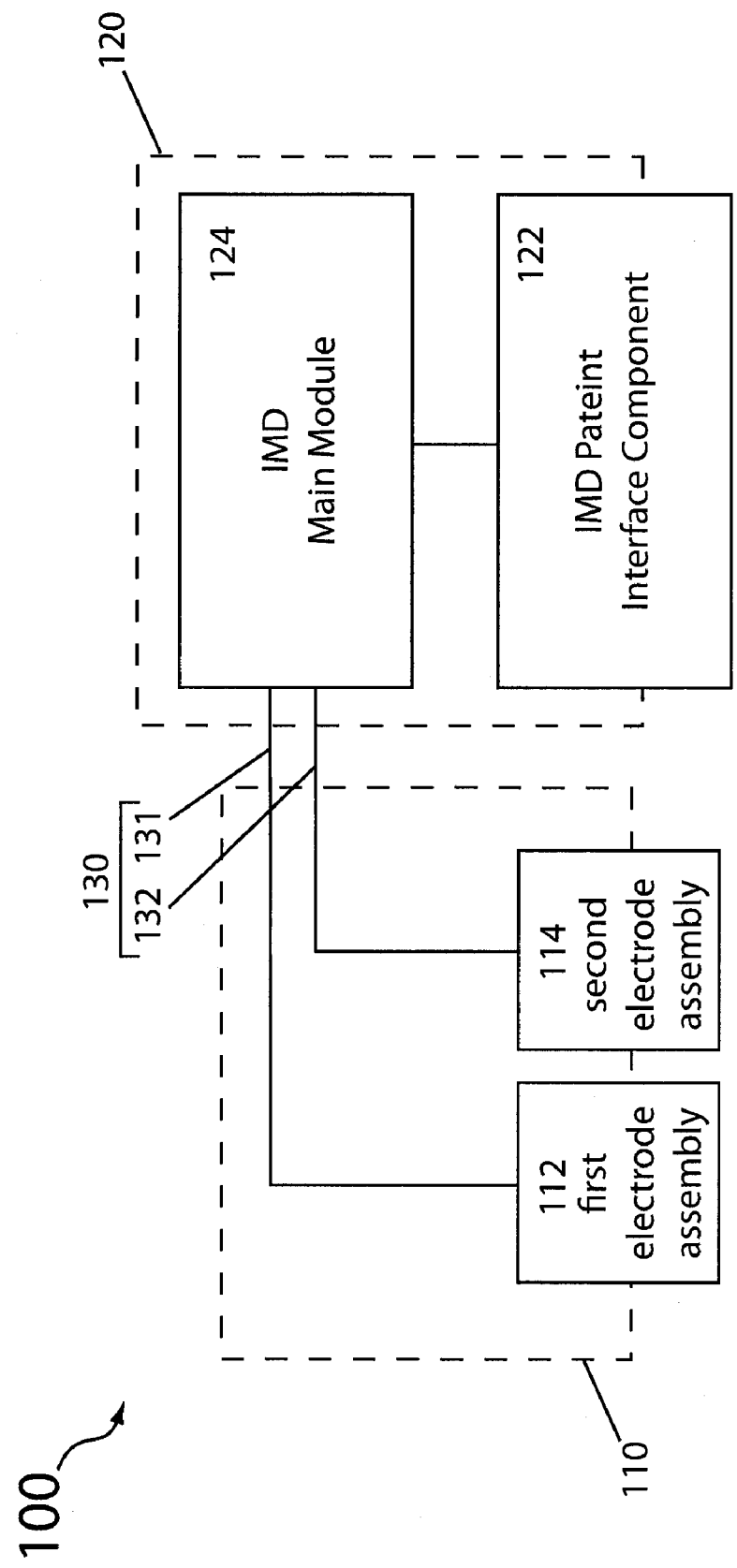
FIG. 1 is a high-level block diagram of an implantable medical device system in accordance with various embodiments of the present invention.

FIG. 1 is a high-level block diagram of an implantable medical device system 100 in accordance with various embodiments of the present invention. The system includes an implantable power cell 110 that provides electrical power to an implantable medical device (IMD) 120, the IMD being a component of the IMD system.

Power cell 110 includes an electrode assembly pair composed of first and second electrode assembly 112/114. The first electrode assembly 112 may be a hermetically sealed anode assembly and the second electrode assembly 114 a cathode assembly.

Prior to or during implantation, the power cell and in particular each electrode assembly is electrically coupled to the IMD. In various embodiments this is accomplished by electrical coupling component 130, which may be a pair of electrical leads (131, 132) encased in its own or a shared biocompatible electrically insulating sheath(s). Leads 131 and 132 are sometimes referred to as power leads for it is their function to carry electrical current for powering the IMD.

IMD 120 may be any implantable device, typically medical, for which electrical power is needed to operate appropriately, including neural or cardiac assistive devices, such as a cardiac pacemaker, cardiac defibrillator, neuro-stimulator (e.g., for deep brain stimulation), drug pump, and cochlear implant. Illustrative examples of these are provided in Table 1, and the patents listed therein are hereby incorporated by reference herein in their respective entireties.

TABLE 1

| IMD | U.S. Pat. No. |
| --- | --- |
| Cardiac Pacemaker | 6,615,083; 5,387,228; 5,447,525; 4,157,720 3,870,050; 3,618,615 |
| Cardiac Defibrillator | 6,647,291; 5,957,956; 4,727,877; 3,397,226 |
| Neuro-stimilator | 6,253,109; 6,301,492; 6,484,059 |
| Cochlear Implant | 5,344,387; 4,762,135; 5,749,912 |
| Drug Pump | 4,898,585; 4,627,832; 4,604,090 |

Practitioners of ordinary skill in the art will appreciate that the devices and methods disclosed in the patents listed in Table 1, or other implantable devices, may be modified advantageously by using the teachings of the present invention, and, in particular, modifying the source of electrical power by replacing or otherwise supplementing it with an implantable electrochemical power cell of the present invention.

IMD 120 includes at least one interface component 122 for interacting with the subject (or patient) in order to provide one or both of monitoring or delivering a therapy. For instance, the interface component may include a sensor and/or a therapy delivery component, such as an implantable tissue-stimulating electrode(s) used in cardiac pacemakers or brain stimulators or cochlear implants. Depending on the application, IMD 120 may further comprise an electronics module 124 containing electronic circuitry for controlling output to the interface component and/or for receiving and processing sensory information, and/or telemetry coils for communicating information to and from an operator, such as a medical practitioner, for controlling device protocols. In known fashion, the electronics module is generally contained inside a hermetically sealed biocompatible enclosure, e.g., a titanium housing. IMD 120 may include other conventional or known IMD components, some of which are described in the patents listed in Table 1, and all of which may be suitably incorporated for use in the IMD system of the present invention. Furthermore, it is to be understood that a person of skill in the art, when describing a conventional IMD, may refer to a patient interface component as a component of the device itself or as a separate component coupled thereto. However, regardless of the manner in which the IMD and its patient interface may be conventionally described, one of ordinary skill in the art will appreciate that within the context of the description provided herein, IMD 120 encompasses the patient interface component but does not encompass power cell 110, which, as a discrete component of IMD system 100, is distinct from that of IMD component 120 itself.

In some embodiments IMD 120 is without an internal energy source, and electrical energy is provided to the device 120 entirely by power cell 110. In other embodiments the main source of electrical energy required to operate IMD 120 is provided by the implantable electrochemical power cell 110. Wherein, by use of the term main source it is meant that the power cell provides more than 50% of the energy necessary to power the IMD system over its anticipated service life, and typically more than 75%, or 90% of the electrical energy is provided by the power cell. In various embodiments power cell 110 may be used to recharge a battery or charge a capacitor. For instance, the capacitor or rechargeable battery (e.g., a high power lithium ion battery), a component of the IMD, may be used to provide a periodic voltage pulse to a stimulating electrode, and subsequently charged by the power cell to enable it to deliver a follow-on pulse (or pulses). In certain embodiments IMD 120 houses an internal rechargeable battery that powers the IMD interface components, and/or module electronics, and the power cell functions as an energy source to recharge the internal battery, periodically, as needed. For instance, an internal rechargeable battery, or capacitor, incorporated in the IMD main module 124 providing the electrical power to drive a stimulating pulse to the subject, and power cell 110 serving to power device electronics, and/or to recharge the internal battery or capacitor, as needed.

Furthermore, while it is illustrated in FIG. 1 that a single power cell provides electrical power to a single IMD, the invention is not limited as such and it is contemplated herein that the power cell is electrically coupled to more than one IMD (e.g., two or three or more), and/or that the IMD system contains a plurality of power cells (i.e., more than one power cell, e.g., two or three or more).

Implantable Electrical Stimulation System

In what follows the power cell of the instant invention and its inventive components (e.g., the hermetically sealed anode assembly) are described in more detail with reference to a particular IMD system embodiment, namely that of an implantable electrical stimulation system, and in a particular illustrative example to that of a cardiac pacemaker system. It is to be understood, however, that the power cell described hereunder, including its components, is not to be construed as limited to those, or that, system specific embodiment(s) or illustrative example.

IMD systems of the present invention may provide one or both of monitoring and/or delivering therapy to a patient (or subject), and may take the form of an implantable electrical stimulation system (i.e., an electrical stimulator) for delivering an electrical stimulating impulse (or series of pulses) to the heart or brain or other tissue or organ of a patient. The system may be a pacemaker, defibrillator, nerve or brain stimulator or the like or some combination thereof.

Figure 2:
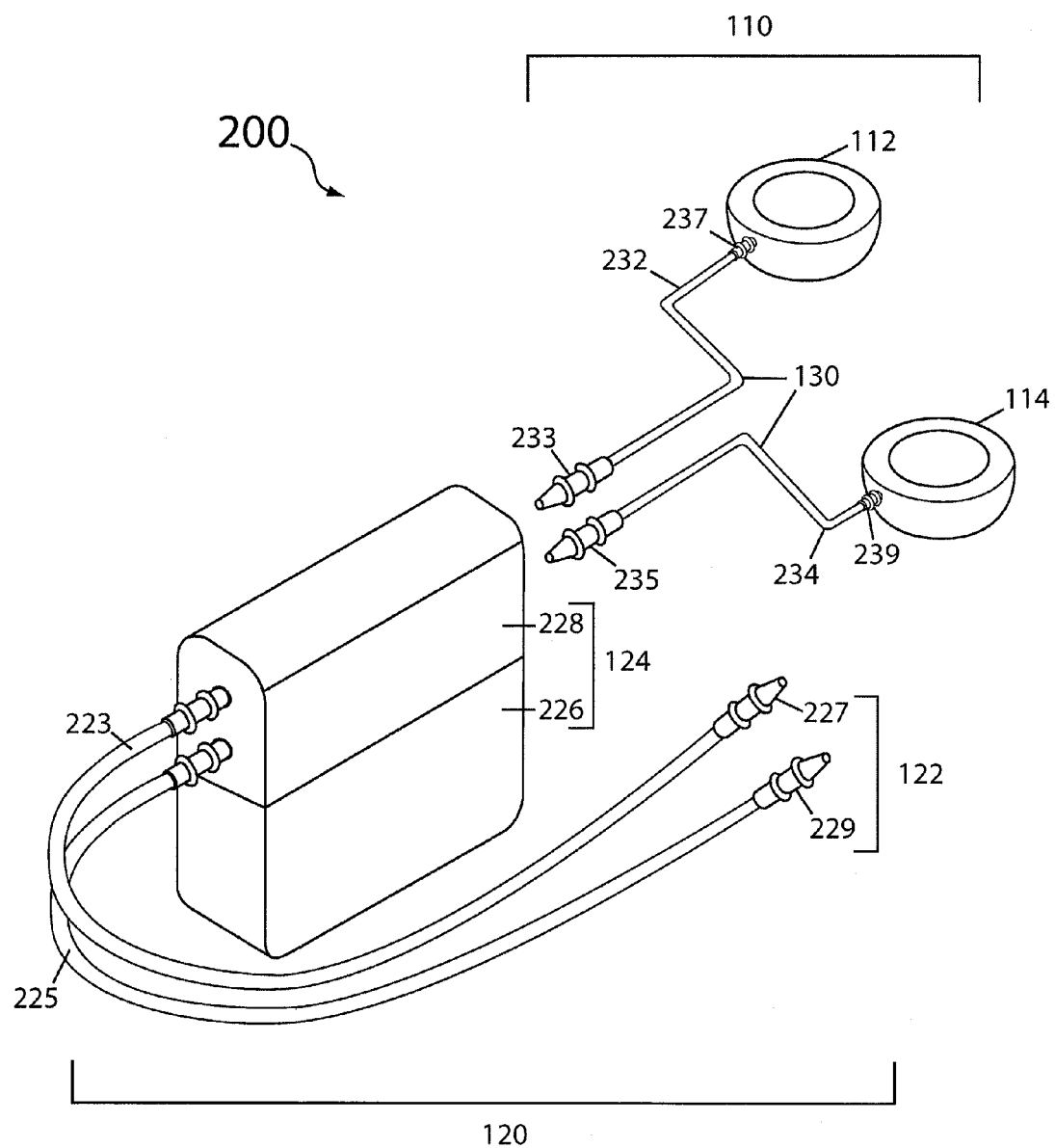
FIG. 2 is a simplified schematic view of one embodiment of an implantable medical device system in accordance with the present invention.

In certain embodiments, the IMD system illustrated in the block diagram of FIG. 1 is an implantable electrical stimulator, as illustrated in FIG. 2. The system 200 includes an implantable medical device 120 electrically powered, in part or in its entirety, by power cell 110 comprising, as described above, an electrode pair assembly consisting of a first electrode assembly 112 and a second electrode assembly 114. The power cell may further comprise an electrical coupling component 130, which may take a variety of forms and is depicted in FIG. 2 as implantable electrical leads 232/234 for coupling, electrically, the IMD to the first and second electrode assembly, respectively. The distal end connected to the IMD and the proximal end connected to its respective electrode assembly. The distal and proximal ends may optionally have end terminals shown as 233/235 and 237/239 for detachable coupling to the IMD and respective electrode assembly.

In various embodiments IMD 120 and one or both of the first and second electrode assembly (112/114) are spatially separated components of the IMD system 100, and though electrically tethered via electrical coupling component 130, the electrodes may be remotely implantably positioned relative to the IMD. Thus providing flexibility in terms of where in the body, or in which body cavity, the components are implanted and their positional configuration relative to each other. For instance the first assembly, an anode assembly, implanted in a first body cavity, and the second assembly, a cathode assembly, implanted in a second body cavity, spatially separated from the first body cavity. In alternative embodiments it is contemplated that one or both of the electrode assemblies may not be spatially separated from the IMD. For instance, one or both of the electrode assemblies may be integrated as part of an exterior wall portion of the IMD housing, thereby mitigating the need for an external power lead or leads, and by this expedient eliminating a potential leakage risk derived from the use of such a connection. Moreover, to facilitate surgical implantation, it is also contemplated herein that the electrode assemblies, first and second, may be mechanically conjoined to form a integrated cell that implanted in a single step may be surgically beneficial when compared to implanting each assembly individually, e.g., one after the other.

Continuing with reference to FIG. 2, IMD 120 has at least one, and commonly two or more, stimulating electrode leads (e.g., as shown, two leads: 223 & 225) that, serving as elements of the patient interface component 122, provide the electrical connection between the IMD and the stimulating electrodes 227/229. The type and construction of the stimulating electrode lead(s) (i.e., biomedeical leads) and biomedical electrodes depends on the type of electrical stimulator and its intended application. Stimulating electrodes and biomedical leads are well known to those of skill in the various IMD art forms, and therefore details concerning them will not be described herein, except to mention that reference can be made to those patents listed in table 1, wherein the reader will find a description of suitable stimulating electrodes, biomedical leads and biomedical connector types. Medical electrical lead wires or biomedical leads are also described in a number of publications including the book Cardiac Pacing and ICD's 4$^{th}$ Edition (2005) by Ellenbogen and Wood published by Wiley & Sons; see especially pages 82-98, incorporated by reference herein.

IMD 120 further comprises a main module 124 (or electronics module) that, in various embodiments, serves the function of an implantable pulse generator (IPG) minus an energy (power) source or its main energy source. The invention, however, is not intended to be so limited, and it is contemplated herein that the IMD, or specifically the main module, may contain its own internal energy source, or sources, and that power cell 110 is incorporated in the system to provide back-up power and/or to power peripheral components (e.g., electronics). In some embodiments IMD 120, and in particular main module 124, houses a secondary energy (or power) source such as a rechargeable battery (e.g., a high power lithium ion battery) or capacitor for which the energy for charge is provided by power cell 110.

Figure 3:
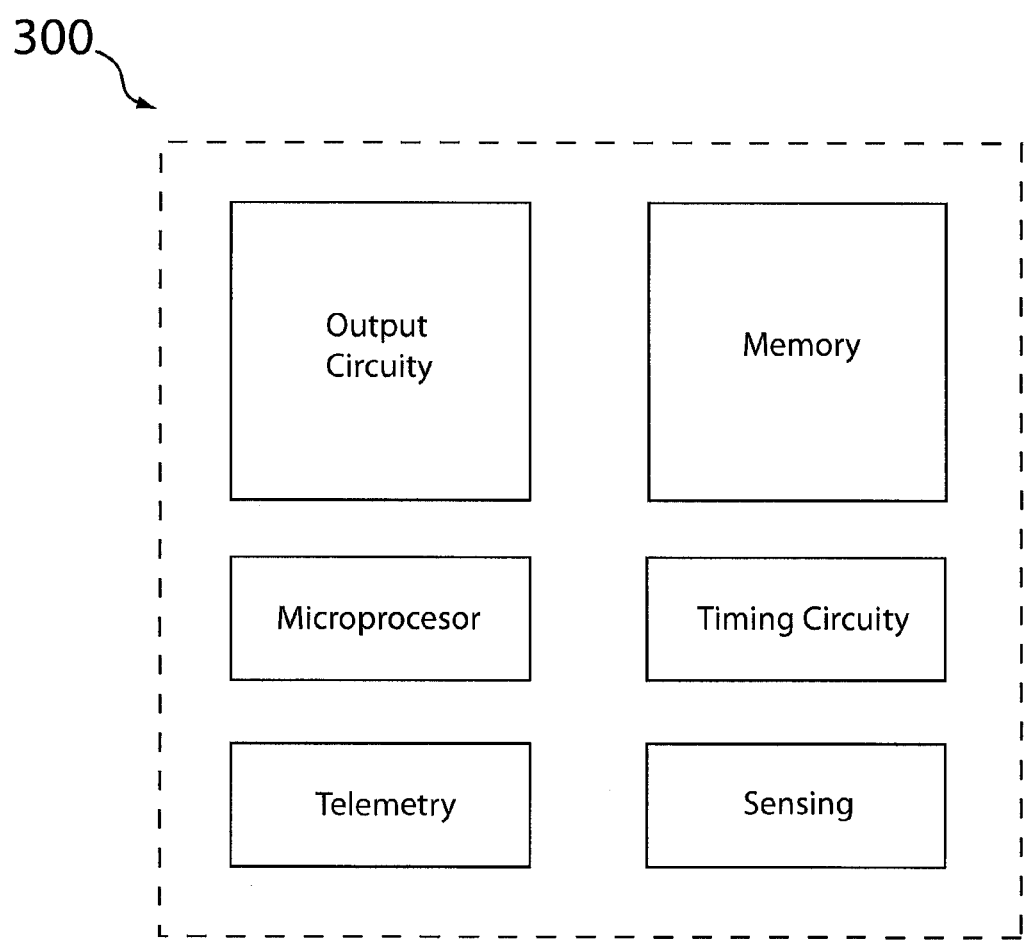
FIG. 3 is a block diagram of an implantable pulse generator in accordance with one embodiment of an implantable medical device system of the present invention, the system a cardiac pacemaker.

Pulse generators for implantable electrical stimulators are known in the art, and are described in the patents listed in Table 1. Details concerning the components and architecture of the IPG will depend on the intended application of the IMD system. Generally, for an electrical stimulator, the IPG contains output circuitry and timing circuitry for controlling the stimulating output pulse as well as signal processing electronics including a microprocessor and memory (e.g., ROM and RAM), and telemetry circuitry (including telemetry coils) for communicating to and from an external programmer; and if the IPG is rate adaptive it may also have sensing components and sensing circuitry (e.g., sense amplifiers) for determining the efficacy of the stimulation and/or for monitoring a response signal. A block diagram 300 of the major physical elements of an IPG suitable for use as a main module for an electrical stimulation system of the present invention, and in particular that for a cardiac pacemaker, is illustrated in FIG. 3. The IPG generally serves to pace and sense, and the functions and further details of the various blocks and their sub-components can be found in the following sources, to mention just a few: Pacemaker and Implantable Cardioverter-Defibrillator Circuitry (Mark W. Kroll and Paul A. Levine); Cardiac Pacing and ICDs (Kenneth Ellenbogen and Mark A. Wood, Fourth Edition). Further detailed descriptions of various types of pulse generators for cardiac pacemakers are found in U.S. Pat. Nos. 3,870,050; 3,618,615; 5,447,525; and 3,508,167. All of the above patents or otherwise are hereby incorporated by reference.

Continuing with reference to FIG. 2, electronic components of IPG 124 are contained in a hermetically sealed biocompatible case 226, generally a hollow housing made of a biocompatible material, typically a biocompatible metal (e.g., titanium). The housing is fitted with a connector block 228 for providing a fluid-tight electrical feed-through for coupling to the stimulating biomedical leads 223/225 and the power leads 232/234 extending from the power cell to the IPG. Connector blocks and biocompatible housings are known in the art for connecting a pacemaker to a stimulating electrode lead, and some are described in U.S. Pat. Nos. 7,376,465; 5,314,451; 5176136; 4,262,673; 4,180,078; 4,112,953, all of which are hereby incorporated by reference in their entirety. And those known connector blocks are also suitable for use herein as connector block 228 when appropriately modified by one of skill in the art for the additional purpose of coupling the power leads 233/235 to the main module 226, e.g., by using two additional bore holes in the body of the block fitted with feedthrough connectors for mating, and preferably detachably mating, with the power leads, one or both.

Implantable Power Cell

Implantable Power Cell

Continuing with reference to FIG. 2, the implantable power cell 110 includes a pair of indwelling electrode assemblies, sometimes referred to herein and in the claims as an electrode assembly pair consisting of a first electrode assembly 112 (e.g., an anode assembly) and a second electrode assembly 114 (e.g., a cathode assembly). The pair is positioned, upon implantation, such that each assembly contacts and electrically interfaces with bodily fluid, and bodily fluid(s) between the assemblies serves as an electrolyte (or electrolytic medium) of the cell. The power cell has an open architecture wherein each of the anode and cathode assembly, not enclosed in a common hermetic enclosure, electrically interface with bodily fluid.

The power cell may further comprise an electrical coupling component 130, for electrically coupling the assembly pair (112/114) to the main module 124, and which may take the form of a pair of indwelling electrical leads 232/234 each having a distal end coupled to the IMD 120 and a proximal end coupled to its respective electrode assembly.

Indwelling electrical leads are generally known in the biomedical device field for carrying electrical stimulating pulses from an IMD to a stimulating electrode, and when used for that purpose are sometimes referred to by those of skill in the art as biomedical leads or implantable medical electrical leads. Electrical leads 232/234, while also indwelling, serve a different purpose herein, which is to carry electrical current for powering the medical device, namely IMD 120, as opposed to carrying electrical current for providing a therapeutic stimulation, and for that reason, such a lead, when used herein, is sometimes referred to as a power cell lead, or more simply as a power lead.

A component of the power cell, coupling component 130 may take the form of an electrical wire disposed in an electrically insulating and biocompatible, generally tubular-like, sheath (e.g., a biocompatible polymer). For example, power lead 232/234 may be composed of a conductor element having an appropriate wire gauge to support the electronic current between the electrode assemblies and an insulating biocompatible outer sleeve element with a bore diameter capable of receiving the wire therethrough, and for isolating the conductor from contact with constituents of the external environment (e.g., internal bodily fluids). The conductor element may be any suitable conductor such as a metal including, but not limited to, stainless steel, titanium and metal alloys including cobalt alloys such as the commercially known alloy MP35N (®) or Elgiloy Medical, typically having a wire-like form. The outer sleeve, biocompatible, resists biodegradation and may be constructed from any number of suitable polymers known in the art, including thermoplastic polyurethane (TPU) and polypropylene, e.g., such as that sold under the trademark PROLENE. Generally, the sleeve will have at least one inner bore in which the conductor element is disposed. Preferably the power lead is flexible. In certain embodiments each power lead may contain two distinct conductor elements to provide a failsafe such that in case one of the leads should lose conductance the other lead remains capable of delivering the electrical current, or if one of the leads should begin to corrode, the other conductor will bear more of the current, thereby allowing the power cell to maintain a low impedance. Medical electrical leads, including their conductor elements and outer sleeves are well known in the art and are suitable for use herein as power lead wires when appropriately modified to meet the electrical demands of the power cell; see, e.g., U.S. Pat. Nos. 5,760,341; 5,483,022; 6,066,166; 7,138,582; 6,720,497; 7,065,411, as well as in the book entitled Cardiac Pacing and ICD's $4^{th}$ Edition (2005) by Ellenbogen and Wood published by Wiley & Sons; see especially pages 82-98.

The power lead may have an end terminal on one or both of their proximal or distal ends for permanent or detachable coupling/de-coupling to/from the IMD and/or its respective electrode assembly; see 233/235 and 237/239 in FIG. 2. For detachable coupling, the referenced body (i.e., the IMD or electrode assembly) is adapted with a matching feedthrough connector for mating with the end terminal. For instance, the power lead end terminal having a male connector pin on one or both its distal and proximal ends and configured thereto for detachable coupling to a connector assembly of the IMD or electrode, such as that which has an appropriately configured female connector for receiving the end terminal pin. A wide variety of techniques and methods have been used over the years to connect medical leads to pacemakers, and they are suitable herein for the above stated purpose of electrically connecting a power lead to an electrode assembly. One example of such an interconnection systems is the VS-1 (voluntary standard-1) connector standard; see for example Calfee et al., "A Voluntary Standard for 3.2 mm Unipolar and Bipolar Pacemaker Leads and Connectors." PACE, Vol. 9, 1181-85 (November-December 1986). Alternatively, the distal end and/or proximal end of the power lead, e.g., when in wire form, may extend through a porthole in the casing of the electrode assembly and there through sealed using a sealant, preferably biocompatible, such as an epoxy resin or thermoplastic polymer (e.g., TPU) or the like.

It is to be understood that the invention is not limited to the manner in which or when the electrical coupling between the power cell and the IMD is made. The power leads, biocompatible, may be permanently or detachably affixed to the IMD and/or electrode assembly, and the act of coupling may be performed during cell or system manufacture or thereafter, such as prior to or upon surgically implanting the IMD. Detachable coupling, be it at the distal or proximal end or both, is advantageous in that it enhances system versatility and may be used to prolong service life by enabling replacement of an electrode assembly or the IMD without surgical removal of the other(s). For instance, as described in one embodiment below, where the power cell is a biological semi-fuel cell, detachable coupling enables replacement of a hermetic anode assembly without removal of the cathode assembly or the IMD itself, which, depending on the application of the IMD, can be very important from the standpoint of patient safety and service life since the power cell can be effectively re-fueled in this manner.

Due to the power cell open architecture, as illustrated in FIG. 2, the first electrode assembly and the second electrode assembly are not affixed to each other, but rather each is electrically tethered, via power leads, to the IMD. Accordingly, the implantable position of the first electrode assembly is unconstrained by the implantable position of the second electrode assembly. Moreover, the implantable position of the electrode assembly is mechanically unconstrained by the implantable position of the IMD, where, however, consideration must be given to the length of the power lead so as to ensure that the IR drop across the lead is not prohibitive.

Hermetic Anode Assembly

Continuing with reference to FIG. 2, the first electrode assembly 112 may be a biocompatible hermetically sealed anode assembly and the second assembly 114 therefore a cathode assembly, e.g., a bio-cathode assembly of which a more detailed description is provided later in the specification.

Figure 4A:
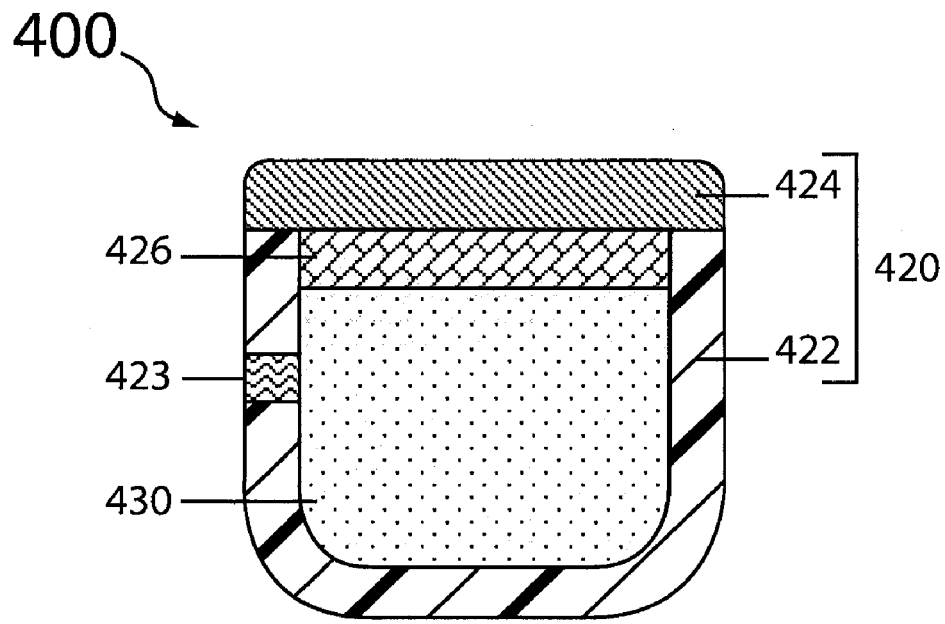
FIGS. 4A-B schematically illustrate a first (4A) and a second (4B) embodiment of an inventive biocompatible protected electrode assembly in accordance with the present invention.
Figure 4B:
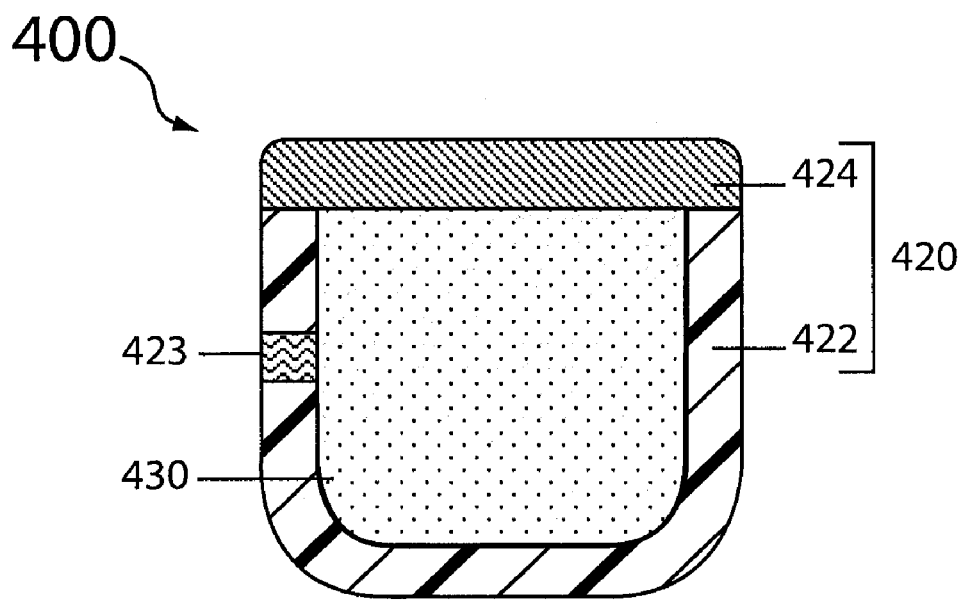

In one embodiment the first electrode assembly is a biocompatible hermetically sealed anode assembly, which, in accordance with one embodiment of the instant invention, is schematically illustrated in FIGS. 4A and 4B. The anode assembly 400A/B may be an alkali metal anode assembly, for instance an hermetically sealed lithium anode assembly comprising an electroactive lithium component material 430 sealed inside, and therefore protected by, a liquid tight (preferably fluid tight) housing 420 having at least one lithium ion conductive active wall member 424, that provides a solid bodily fluid impermeable medium through which lithium ions electrically migrate out of the housing during cell discharge.

The anode assembly 400A/B may take on any suitable geometric form and is sized, both in terms of its charge capacity (ampere-hours, Ah) and physical dimensions, according to the application in which the power cell is employed. The housing 420 (also referred to as an enclosure or compartment) in which the electroactive component material 430 is disposed, and therein isolated from contact with bodily fluid, may be defined by a receptacle member 422 having an open end which is closed off by the active wall member 424 suitably sized for sealing around the open periphery.

The receptacle member 422, bodily fluid impermeable, may take any shape. Generally it has a smooth external surface with smooth contours and corners to enhance its acceptability within the body. It may be a unitary structure, such as a titanium capsule or otherwise cup shaped structure; for example, a capsule machined from a solid piece of metal or deep-drawn from a piece of sheet metal. It is also contemplated that the receptacle may be defined by conjoining multiple wall members, typically inactive wall members. The receptacle has a biocompatible exterior surface and an interior surface that is chemically compatible with internal constituents that it comes into contact with, which may include, in certain embodiments, the electroactive component material (e.g., lithium metal) and/or, in some embodiments, a liquid, gel or polymer electrolyte. To prevent electrical shorting, the receptacle member in a direction across its thickness is preferably electrically insulating. For instance the receptacle inner surface composed of a chemically inert and/or electronically insulating material, such as a suitable polymer, e.g., polyethylene.

The receptacle, unitary or otherwise, may be made of a single material that meets the requisite compatibility, insulating and barrier requirements as described above, such as polyethylene, polypropylene, or stainless steel, titanium or other suitable materials which are substantially inactive in the human body. Or it (the receptacle) may be a layered composite having an inner layer compatible with the internal assembly constituents and an outer biocompatible layer. Additional layers are contemplated herein between the inner and outer layers to enhance chemical compatibility and, more generally, overall device performance. This includes a middle layer, such as a metal layer, e.g., titanium, that imparts excellent barrier properties against the ingress of bodily fluids and the like, and which, itself, may also have excellent biocompatibility. A suitable receptacle member may be composed of a titanium metal layer (or sheet) as the outer layer and an inner polymer layer (or sheet) such as polyethylene facing, and possibly contacting, internal constituents of the compartment. The outer layer of the receptacle may also be coated with a biocompatible material (typically a polymer layer such as a polyurethane, as is known in the IMD art to enhance resistance against biodegradation. The receptacle is also of sufficient thickness to provide a mechanically robust enclosure (it may be rigid or flexible, typically rigid), and to achieve its intended purpose of isolating (i.e., protecting) the electroactive component material from adversely contacting bodily fluids and, similarly, to prevent leaking out of internal assembly constituents, and in particular to prevent egress of liquids (e.g., non-aqueous solvents) which, as discussed later, may be used in the housing as a lithium ion conductive interlayer electrolyte between the lithium metal and the interior surface of the active wall member. Generally the receptacle is constructed of a rigid material, but it is contemplated herein that the receptacle may be flexible or even compliant to changes in the lithium thickness. Compliant seal structures are described in US Pat. Pub. No.: 20070037058 and may be used herein as a receptacle member when appropriately modified to ensure biocompatibility, such as by using materials and methods known in the IMD arts; e.g., coating the exterior surface with a biocompatible polymer.

To allow passage of electrons into or out of the housing it is necessary to penetrate the receptacle wall with one or more electrical leads so as to provide electrical access to the electroactive component material, for example via a feedthrough connector 425 that penetrates the receptacle wall but maintains the hermetically sealed environment. There are numerous methods and techniques known to those of skill in the art for penetrating a hermetic enclosure with an electrical lead, including the use of feedthrough connectors, and it would be extraneous to elaborate in detail on all of them here. Accordingly reference is made to some of them, including that which is described in U.S. Pat. Nos. 5,851,222; 4,940,858; 5,817,984; 6,844,502; and 5,643,694, all of which are hereby incorporated by reference. Preferably the feedthrough connector 425 is configured to detachably mate with its associated power lead 232, thereby allowing the electrode assembly to be removed, independently, without necessitating surgical removal of one or more of the power lead, IMD or cathode assembly. Alternatively, electrical access may be of a more rudimentary nature whereby the power lead is sealed about a porthole in the receptacle wall, and therewith permanently affixed using an epoxy, typically biocompatible or otherwise coated with a biocompatible compound. It is also contemplated herein to use a connector block assembly affixed to an inactive wall member or receptacle; for example, a connector block assembly similar to that described above for receiving the distal end of a power lead.

The active wall member 424, impermeable to bodily fluids, provides a solid medium through which lithium ions migrate out of the compartment during cell discharge. Accordingly the active wall member, conductive of lithium ions, allows lithium ions to pass through it under the influence of an electric field and has no through porosity or other defects that would allow bodily fluid or moisture from the ambient air to permeate, flow, seep, or otherwise pass through it.

On one side the active wall member has an exterior surface that, facing and exposed to the external environment, is substantially biocompatible with bodily fluids that it comes into contact with whence implanted, and that surface also chemically compatible in contact with ambient air. During device operation, the exterior surface contacts and electrically interfaces with bodily fluids thus allowing egress of lithium ions from the compartment during discharge. On the opposite side, the active wall member has an interior surface facing inside the compartment and, exposed therein, is chemically compatible in contact with constituents of the anode compartment that it comes into contact with, which may include, in some embodiments, the electroactive component material or, in other embodiments, liquid, gel or solid polymer electrolytes, such as aprotic organic solvent based electrolytes.

The active wall member, active in the sense that it provides the electrochemical function of providing a passageway for the egress of lithium ions out of the compartment, has sufficient lithium ion conductance to support the electrical current of the cell without giving rise to unduly large impedance. The conductivity of the active wall member is preferably greater than $10^{-6}$ S/cm, more preferably greater than $10^{-5}$ S/cm, even more preferably greater than $10^{-4}$ S/cm or $10^{-3}$ S/cm. Where the application or use requires low currents, the active wall member may be constructed with exceptional thickness to enhance its mechanical strength; for instance, the active wall member may have a thickness of between 500 μm and 1 mm; or 1 mm and 2 mm; or between 2 mm and 5 mm; or 5 mm and 1 cm, or thicker, e.g., greater than 1 cm.

In accordance with the invention, the active wall member has both barrier and conductive properties. When used in a hermetic lithium anode assembly, the active wall member: 1) conducts lithium ions and allows lithium ions to pass through it via electrical migration; 2) provides a barrier against the through transmission of bodily fluids and water; and 3) is chemically compatible in contact with ambient air and substantially biocompatible in contact with internal bodily fluids on a side facing the external environment.

The active wall member may take the form of a lithium ion conductive monolithic mass of uniform or varied composition or it may be a laminate of different Li-ion conducting layers having discrete or gradual interfaces there between. Compositional variation, be it derived from a laminate or otherwise, can be advantageous, or necessary, for improving interfacial properties between the exterior surface of the wall member and bodily fluid, or between the interior surface and internal constituents of the compartment, or to enhance the overall conductance of the wall, and/or e.g., to allow for an increase of the active wall thickness by making use of a highly conductive bulk composition. While there is generally no limit to the number of layers or the degree of compositional variation, it is generally preferred from a manufacturing, cost and reliability perspective to keep the structure as simple as possible, and so, for this reason, if a single composition (e.g., a monolithic mass of uniform composition) can be used it is certainly preferred.

In various embodiments the lithium ion conductive active wall member is inorganic and its chemical makeup may be that of a single or multiple inorganic compound(s) of a crystalline, such as polycrystalline, (e.g., ceramic or glass ceramic) and/or amorphous (e.g., glass) solid. While not intending to be limited by the manner in which the active wall member is fabricated, it is typically a sintered or melt-processed mass, such as a plate or pellet or otherwise material chunk of desired dimensions suitable to achieve, in thickness, the necessary mechanical strength and, in area, an acceptable conductance to support the cell current. In certain embodiments the wall member is composed entirely of crystalline inorganic compounds (typically polycrystalline), and in a preferred embodiment the wall member is of a single composition, inorganic and polycrystalline.

Taking advantage of their biocompatibility, compounds of titanium and/or that of phosphates are particularly suitable for defining the exterior surface composition of the active wall member, or for that matter, its bulk composition. Accordingly, in various embodiments the active wall member is a lithium ion conductive titanium or metal phosphate compound e.g., titanium phosphate, niobium phosphate, zirconium phosphate, hafnium phosphate, and preferably a lithium titanium phosphate compound, such as $LiTi_2(PO_4)_3$ and derivatives thereof such as $LiAl_{0.3}Ti_{1.7}(PO_4)_3$ and the like, or a lithium oxide compound such as titanium oxide compound, for instance that of the type $LiLaTiO_3$, or a lithium garnet conductor of the type e.g., $Li_5La_3M_2O_{12}$ (where M is Nb or Ta), or sillicates, especially lithium silicate glasses, and which, in reference to the above compositions, may be melt processed or, preferably, sintered, or both melted and sintered, the most suitable process depending on the particular composition.

Methods of making glass, glass ceramic or ceramic materials, e.g., in pellet form, and in particular those of lithium titanium phosphate, lithium titanium oxide and lithium garnets are described in patents and in the general literature, including U.S. Pat. No. 4,985,317; U.S. Pat. No. 5,702,995; U.S. Pat. No. 6,030,909; and US Pat. Pub. No.: 20100203383, all of which are hereby incorporated by reference in their entireties. To ensure that the pellet (or plate), or more generally a material chunk, is dense or otherwise has no through porosity, techniques such as those for filling through holes may be used herein for that same purpose; see e.g., US Pat. Pub. No.: 2007/0172739 which is hereby incorporated by reference.

To form or otherwise enclose the anode compartment, the receptacle's open end may be hermetically closed-off by sealing the active wall member 424 to the periphery of the receptacle about, or generally in the proximity of, the opening. The shape and size (i.e., the physical dimensions) of the wall member is generally constructed, in part, to ensure a proper seal. The active wall member may be directly sealed to the receptacle, or additional receptacle component materials may be used to enhance the seal or facilitate the sealing process, such as, but not limited to, a sealing ring or annulus set between the outer circumference of the active wall and the inner circumference of the receptacle's opening.

The electroactive component 430 is the material of the anode that electro-oxidized during discharge releases ions to maintain its state of charge neutrality; for example, when the assembly a lithium anode, the ion released from the electroactive is lithium, and lithium ions electrically migrate out of the compartment via the active wall member during cell discharge. Disposed in the hermetic housing, an important feature of the invention is derived from the isolation that is afforded the electroactive component from direct contact with bodily fluids, which enables the use of bodily fluid incompatible electroactive materials having large negative electrochemical potentials that in conjunction with an appropriate cathode enables relatively high and stable cell voltages beyond the electrochemical voltage stability window of water or the bodily fluid in contact with the anode assembly and/or the bodily fluid serving as the electrolytic medium (electrolyte) between the pair of electrode assemblies.

Particularly suitable electroactive lithium materials include lithium metal, lithium metal alloys, lithium intercalation materials, e.g., lithium metal. The lithium materials may be constructed in various forms depending on the size, or capacity, of the power cell in which they are to be utilized. One of skill in the lithium battery art is familiar with various constructions of electroactive lithium, including sheets, films, foils, sinters, blocks and coatings, with or without a current collector attached to it. For example, in one embodiment where high cell capacity is needed the lithium electroactive component is a lithium metal sinter or thick lithium metal foil. The thickness of the electroactive lithium, as measured from a first side opposing the active wall member to a second opposite side, depends on device application and generally is constructed according to the rated ampere-hour capacity of the cell, e.g., lithium metal having a thickness greater than 2 mm, greater than 1 cm, or greater than 2 cm may be used.

Sealed within the anode housing, the electroactive lithium component is configured for lithium ion communication with the active wall member, and this may be accomplished using various strategies. For instance, the electroactive lithium (e.g., lithium metal) may be disposed in direct and intimate contact with the interior surface of the wall member, such as by physical vapor deposition of the metal, melt forming or pressing the metal on the interior surface, among other viable methods. However, depending on the choice of electroactive lithium and the interior surface composition, it may be prudent, and often is, to incorporate there between a lithium ion conductive interlayer that provides or otherwise improves interfacial stability.

The interlayer may be a solid lithium ion conductor stable on its respective sides to the active wall member and the lithium metal. The use of an interlayer may be critical in certain circumstances where the electroactive lithium and the active wall member are chemically incompatible in contact. Various interlayer types may be used, including solid inorganic or organic materials e.g., LiPON or a solid polymer electrolyte such as Li-PEO (e.g., Li salt dissolved in polyethylene oxide polymer and co-polymers); gel electrolytes composed of a solid phase imbibed with a liquid phase; as well as porous or otherwise swellable material layers (e.g., a porous polymer or porous inert ceramic layer or swellable polymer membrane) impregnated with a lithium ion conductive liquid or gel phase electrolyte, typically organic (e.g., aprotic liquid electrolyte).

Particularly suitable solid lithium ion conducting interlayer materials include lithium phosphorous oxynitride based glasses, lithium metal sulfides, lithium metal phosphorous sulfides, and lithium metal halides. Specific examples include lithium nitride (e.g., $Li_3N$), lithium phosphide (e.g., $Li_3P$), lithium iodide (e.g., LiI), lithium bromide, (e.g., LiBr), $Li_2S$—$P_2S_5$, $Li_2SP_2S_5$-LiI, and LiPON. These materials may be applied to the interior surface of the active wall member and then lithium metal may be applied onto these materials, or they may be formed in situ by contacting precursors such as metal nitrides, metal phosphides, metal halides, red phosphorous, iodine, nitrogen or phosphorous containing organics and polymers, and the like with lithium.

Gel electrolytes and liquid electrolytes suitable for use in, or as, the interlayer include those generally useful as electrolytes in lithium metal or lithium ion batteries. Particularly suitable electrolyte solvent and salt combinations that compatible with lithium metal are known to those of skill in the lithium battery art field, and these include aprotic organic solvents such as organic carbonates, ethers, lactones, sulfones, etc., and cominations thereof, such as EC, PC, DEC, DMC, EMC, 1,2-DME or higher glymes, THF, 2MeTHF, sulfolane, and combinations thereof; and suitable salts: $LiPF_6$, $LiBF_4$, $LiAsF_6$, $LiSOCF_3$, or $LiN(SO_2C_2F_5)_2$. When in the gel phase, gelling agents such as polyvinylidene fluoride (PVdF) compounds, hexafluropropylene-vinyldine flourie copolymers (PVdF-HFP), polyacrylonitrile compounds and polyethylene oxide compounds. One particular type of suitable porous interlayer material are semipermeable membranes such as microporous polymers, e.g., porous polyolefin separators such as polyethylene or polypropylene layers about 25 microns thick, which are well known in the lithium metal battery art form, such as are available from Celgard, Inc. Liquid and gel electrolytes suitable for use herein as or as a component of the interlayer electrolyte include those described for use as an anolyte in U.S. Pat. No. 7,282,295 hereby incorporated by reference for all it contains. It is also contemplated herein that the interlayer may be formed by configuring the electroactive lithium in juxtaposition with the wall member to have a spatial separation, filled or otherwise containing a sufficient amount of liquid electrolyte to impart ionic communication, the liquid in contact with the electroactive component material and the interior surface of the active wall member.

In construction the electroactive component material (e.g., a chunk of lithium metal) may be inserted into the receptacle, through the opening, followed by placing a porous interlayer material (e.g., a micro-porous membrane) onto the lithium metal surface facing the receptacle open end, and thereupon dispensing a lithium ion conducting liquid electrolyte for absorption into the pores of the separator. The active wall member then sealed about the periphery of the receptacle open end in a manner to ensure that its inner surface intimately contacts the separator layer, and therein, as well, the impregnated liquid electrolyte. Alternatively, the liquid electrolyte may be incorporated into the compartment subsequent to sealing the active wall member to the receptacle, by dispensing the electrolyte through a porthole and allowing the liquid electrolyte to seep into the pores or otherwise swell the semi-permeable membrane (e.g., to form the gel electrolyte). Thereafter, the porthole may be hermetically closed off, such as by using a sealant, e.g., a biocompatible epoxy. The electrolyte (liquid or gel) may be dispensed in excess beyond that volume necessary to fully impregnate or fill all the pores of the interlayer, thereby providing a reserve of electrolyte, which, over time, may be useful for enhancing the ionic communication between the active wall member and/or electroactive component material. Moreover, for that same purpose, an expandable member, not shown, may be disposed between the electroactive component material and the closed receptacle end to enhance ionic communication over the service life of the assembly, for instance a compressed spring positioned adjacent to the closed end.

Hermetic sealing of the wall member to the periphery of the receptacle's open end may be accomplished by any suitable sealing method, the appropriate method depending on the type of materials being sealed. There are numerous techniques and sealants for making the seal, and these are generally known in the sealing art forms, including glass to metal seals, ceramic/ceramic seals, heat sealing, and sealants including ceramic, glass, metal, epoxy or thermosetting polymers. To enhance chemical resistance against biodegradation the sealant(s) may be covered with a biocompatible coating or layer, such as thermoplastic polyurethane or silicone rubber.

In certain embodiments the anode assembly may be formed by incorporating methods and techniques, and using materials, which are fully described in applicant's patents and co-pending published patent applications, including U.S. Pat. Nos. 7,282,295; 7,390,591; 7,282,302; 7,282,296. In those patents lithium ion conducting structures are described which, e.g., protect at least one major surface of lithium metal from exposure to and contact with the external environment. One of skill in the art will recognize that the protection strategies and methods of fabrication described therein are useful herein for protecting a major surface of the electroactive component material and also for providing an active wall member and an interlayer between it and the lithium.

It is a feature of the instant invention that the isolation provided by the hermetic housing enables the use of electroactive anode materials with exceptionally large negative electrochemical potentials, which would otherwise, in direct contact with bodily fluid, be entirely precluded by their incompatibility in contact with water, e.g., lithium metal. One advantage is, of course, that a high voltage, both open circuit and working, may be generated that, depending on the choice of cathode, is greater than the reduction potential of water or that of bodily fluids in contact with the anode assembly or that which serves as an electrolytic medium between the electrode assembly pair, including voltages greater than 1.5, 2.0V, 2.5V and 3.0V. Another advantage of using a lithium anode assembly is that it makes practical the use of bodily fluid oxygen as an electroactive species of the cathode, where its practicality is otherwise precluded by the overpotential of the cell reaction which in combination with an otherwise low open circuit potential generates impractical working voltages that are less than 1.5 V and more likely less 1 V. e.g., when bodily fluid oxygen is contemplated for use in conjunction with anything other than an anode of sufficiently large negative electrochemical potential, such as magnesium metal which has a high surface impedance that effects a very large IR drop across its active surface, and ultimately a low working voltage.

Accordingly, in various embodiments the invention is directed to a particular type of power cell device, a biological lithium semi-fuel cell, named as such because the anode assembly is lithium based and the cathode assembly is a bio-cathode where the active species, harnessed directly from internal bodily fluid, is effectively a biological fuel of infinite supply, including but not limited to dissolved oxygen and other bodily fluid constituents, preferably dissolved oxygen.

Power Cell is a Biological Lithium Semi-Fuel Cell

In accordance with various embodiments of the invention, power cell 110 may be a biological lithium semi-fuel cell having a first hermetically sealed lithium anode assembly and a second assembly, a bio-cathode assembly, described now in more detail below.

Bio-Cathode Assembly

Figure 5A:
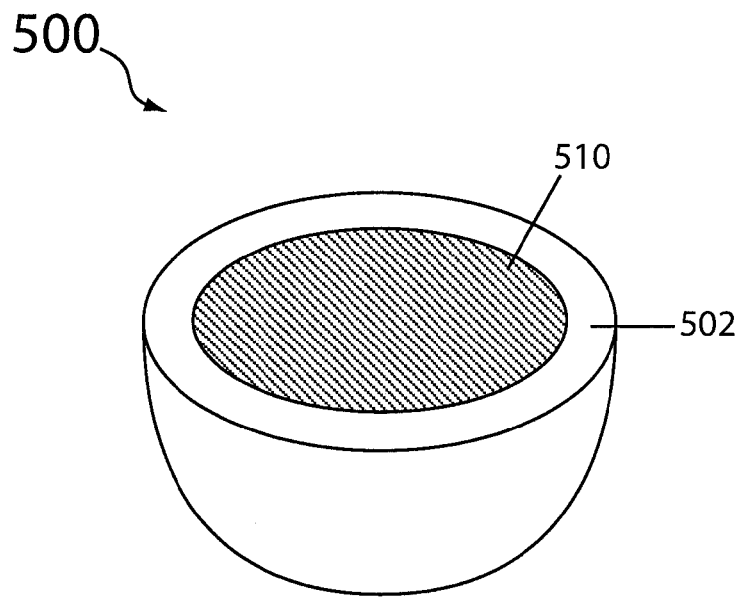
FIGS. 5A-B schematically illustrates one embodiment of a cathode assembly in accordance with the present invention, 5A shows the assembly in a front perspective view and 5B shows it in cross section.

With reference now to FIG. 5, in accordance with the invention, a bio-cathode assembly 500 is illustrated which makes use of an internal bodily fluid constituent as the electroactive species reduced at the cathode during cell discharge. Sometimes referred to as a bodily fluid oxidant or active cathode reagent, the electroactive cathode species may be the only reagent partaking in the discharge reaction at the cathode or it may be used in conjunction with other actives, derived from bodily fluid or not. In one embodiment the active cathode reagent is water or water is the predominating cathode active species, and the semi-fuel cell, in these instances, may be considered a biological Li/water semi-fuel cell. In a preferred embodiment, however, the active reagent is oxygen, or is predominately oxygen, and the semi-fuel cell is a biological lithium/oxygen semi-fuel cell. Dissolved oxygen has several advantages as an electroactive including a highly positive electrode potential and a substantially bio-acceptable discharge product, which in the course of discharge is released into the body.

Continuing with reference to FIG. 5, the bio-cathode 500 includes an electron transfer medium 510 that provides a surface on which, e.g., oxygen derived from within the body (and typically oxygen dissolved in bodily fluid) may be reduced during cell discharge. Accordingly, the bio-cathode assembly, whence implanted, is positioned to ensure that the electron transfer medium electrically interfaces with bodily fluid. Preferably the cathode assembly is positioned within a region of the body, or a body cavity, for which more than, but no less than, a sufficient amount or supply of bodily fluid is available as a fuel source.

The bio-cathode may simply be a biocompatible electron transfer medium such as an electronically conductive material substrate on which oxygen may be electro-reduced on one or both sides, including biocompatible metals, such as platinum or titanium metal, or a carbonaceous material medium with or without a catalyst for stimulating the reaction, depending on the current demanded by the particular application.

The edges, corners and backside of the electron transfer medium 510 may be encased in a biocompatible sheath 502 constructed to enhance the bio-acceptability of the assembly as a whole and to improve the uniformity of the electrochemical reaction at the cathode, for instance by minimizing stray electrochemical effects which can develop near edges and corners. The protective sheath may be made from any suitable biocompatible material, including, but not limited to, polymers and glasses, and even metals or ceramics, preferably electrically insulating, e.g., TPU. For instance, the bio-cathode may simply be a platinum wire or other suitable metal plug embedded in a biocompatible sheath; for example, by potting the wire or plug in a biocompatible polymer resin or glass or ceramic.

Figure 5B:
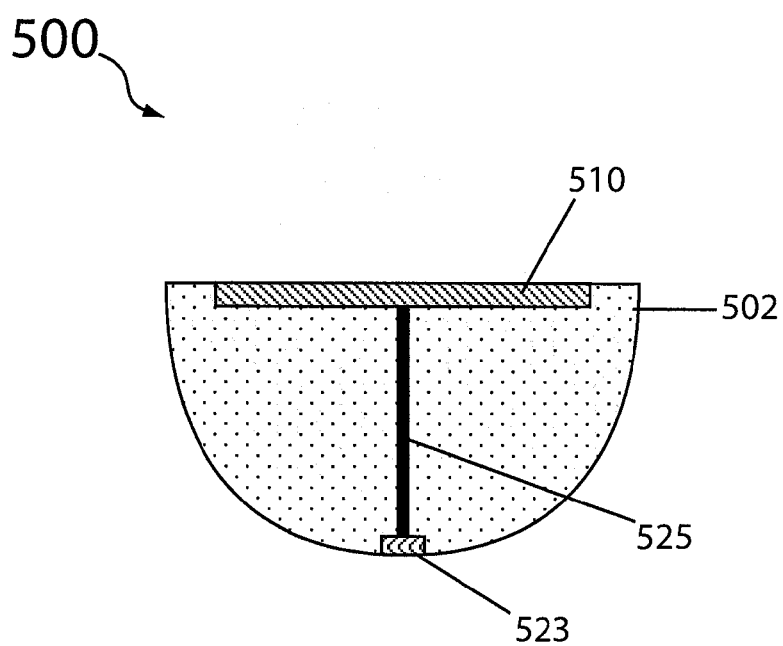

The sheath may include, as illustrated, a feedthrough connector 523 for the purpose of coupling a power lead to the electron transfer medium. For instance, the connector may be electrically coupled, e.g., via wire 525, to the electron transfer medium 510, as shown in FIG. 5B. Feedthrough connector 510 may be of similar if not identical construction to that described above with respect to the anode assembly, and configured for mating, preferably detachably, to a power lead, also as described above for the anode assembly.

In certain embodiments the electron transfer medium may be that which is used as an oxygen electrode in PEM fuel cells, appropriately modified for biocompatibility. PEM cathodes are known in the art, and generally comprise a current collector screen coated with a platinum black and/or carbon black layer. Optionally, catalysts may be added to the cathode coating or otherwise incorporated in the chemical makeup of the electron transfer medium, as necessary, to increase or otherwise enhance the selectivity of the cathode for reacting with oxygen as opposed to it (the cathode) transferring electrons to some other potential reactant in the bodily fluid, which may lead to a lowering of the overall cell potential, or otherwise less desirable.

For applications in which only low current is required, the structure of the cathode can be very simple, including it having a planar, and preferably even a smooth, surface or it may be slightly corrugated to increase its active area, if needed. If larger currents are demanded, the surface area may be augmented to increase the reaction kinetics, e.g., the electron transfer medium constructed of a foam, or mesh, or porous material, such as a felt or carbon or metal paper optionally coated with nanometer or micron sized particles of carbon black or platinum black.

Implantable cathodes which have been described for use in bio-autofuel cells or in bio-galvanic cells, and which are suitable for use herein as an electron transfer medium, are described in U.S. Pat. Nos. 3,897,267; 4,294,891; 3,941,135, all of which are hereby incorporated by reference. Moreover, the construction and use of various implanted cathodes are described in Medical and Biological Engineering published January 1974 pgs. 50-56 by O. Z. Roy and R. W. Wehnert, entitled "Improvments in biogalvanic energy sources"; and in Med. & boil. Engng Vol. 6, pp. 503-516, 1968 entitled "Study of Power Generating Implantable Electrodes" by H. Massie et al, both of which are also hereby incorporated by reference.

Various Power Cell Configurations

Figure 6:
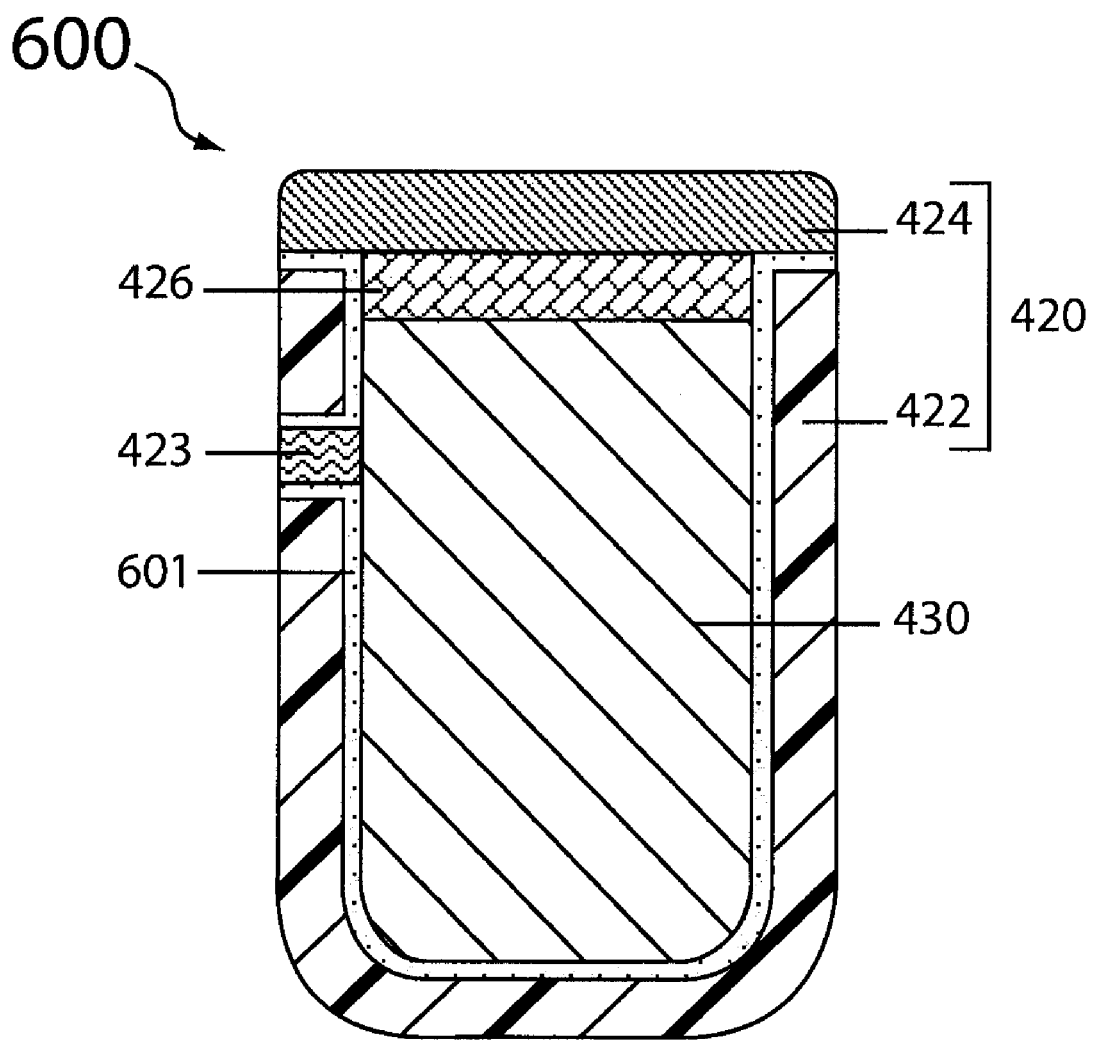
FIG. 6 schematically illustrates one embodiment of an integrated power cell in accordance with the present invention.
Figure 7A:
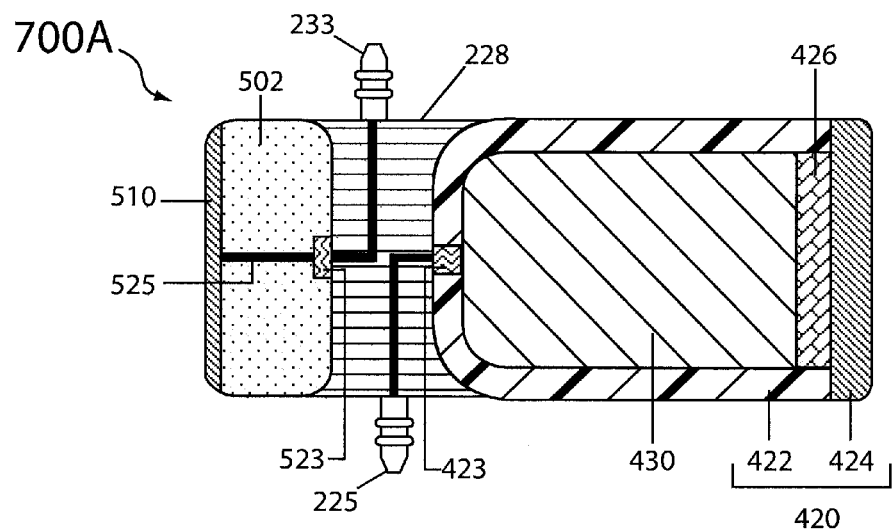
FIGS. 7A-B schematically illustrate embodiments of an integrated power cell in accordance with the present invention.
Figure 7B:
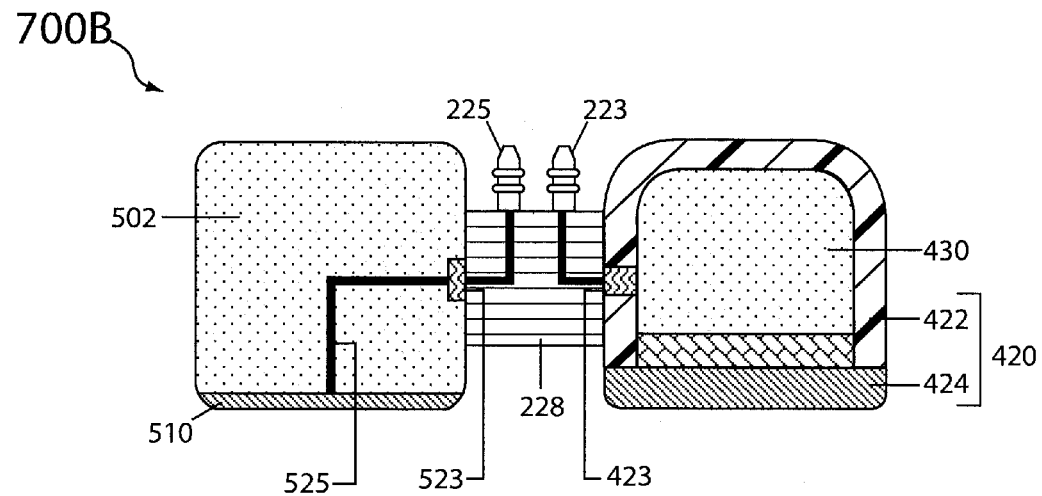

For some applications it may be beneficial to conjoin the anode and cathode assembly in what is termed herein an integrated-cell or integrated-cell configuration; some examples of which are illustrated in FIGS. 6 and 7A-B. In FIG. 6 the cathode assembly defines the outer shell of the anode assembly and more specifically the housing in which the electroactive component material is disposed. By this expedient the anode housing 422 exterior surface provides the electron transfer medium of the cathode. For instance the housing formed from a titanium capsule, as described above, but also including an insulating layer 601, e.g., made of polyethylene or polypropylene, that prevents short circuiting between the electroactive component material 430 and the titanium metal case. The exterior facing titanium surface may provide, by itself, the electron transfer medium, or it may be coated with a high surface area carbon where higher rate performance is desired. It should be appreciated that the entirety, or otherwise nearly all, of the titanium surface may be used for this purpose, or otherwise just that portion necessary to support the cell's electrical current. In other embodiments, as illustrated in FIGS. 7A-B, the integrated-configuration may include a block connector 228 that, as described above, electrically interfaces with but also is mechanically joined (affixed) to one or both of the anode and/or cathode assembly; for example, where the cathode sheath and anode housing are joined/affixed to the block, be it through a mechanical connector (e.g., such as a snap member), the electrical feedthrough connector, or via an epoxy bond.

As mentioned above, while the power cell may have one or both electrode assemblies attached to or integrated as part of the exterior wall portion of the IMD housing, the open cell architecture affords a great deal of flexibility in terms of the position of the anode assembly relative to the cathode assembly, and especially for those embodiments wherein the anode and cathode assemblies, though both electrically tethered to the IMD (e.g., via power leads), are otherwise physically unconstrained relative to each other, and therefore capable of being independently positioned when implanted. This freedom is also provided for in the case of an integrated cell configuration; for instance, in FIGS. 7A-B the electron transfer medium is not disposed in a face-to-face relationship with the active wall member; in FIG. 7A the two active surfaces oppose each other and in FIG. 7B they are arranged in a side-by-side configuration, or some combination thereof may be utilized and it is contemplated herein that the block component is configured with a swivel member that allows the anode and/or cathode to be independently rotated horizontally and/or vertically, thus the cell featuring an on the fly adjustment in two or three dimensions.

Purely from the perspective of cell impedance, it is most efficient to position the anode assembly opposite the cathode assembly, with the active wall member slightly separated from, but in face-to-face relation with, the electron transfer medium. However, it is to be understood that other factors may be taken into consideration including, above all else, the functionality of the device itself and the current to be drawn from the cell in powering the device. And while a face to face relationship may effect the most efficient electrochemical design, other factors may outweigh it, such as the availability of dissolved oxygen to the cathode assembly or the biocompatibility of the anode assembly in a particular cavity. Accordingly, alternative configurations are contemplated wherein the active surface of the electron transfer medium is not disposed in a face to face relation with the active wall member, and as a consequence the electric field lines may take on some curvature, as opposed to a straight path length.

Cardiac Pacemaker Implantable Medical Device System

The biological lithium semi-fuel cell of the present invention is particularly suitable for its application as a power source for cardiac pacers, where it also enables a novel pacemaker construction and novel dual use application.

Figure 8:
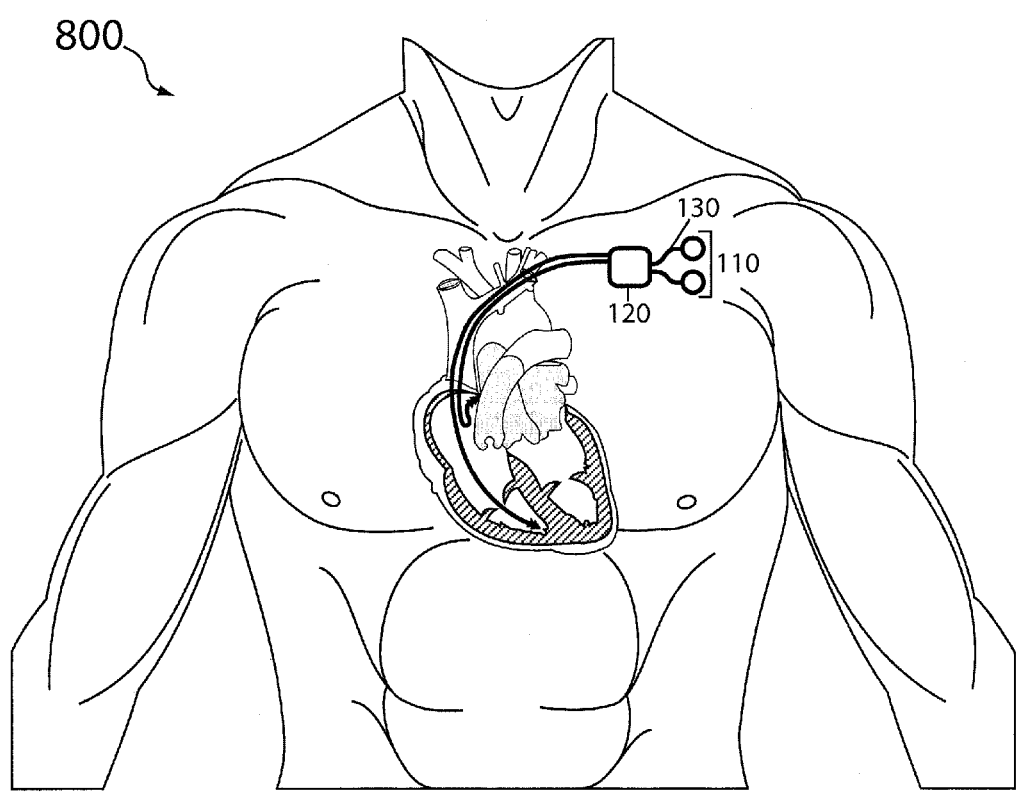
FIG. 8 shows a conceptual drawing of one embodiment of an implantable medical device system in accordance with the instant invention; the system, a cardiac pacemaker, implanted in the body of a patient.

FIG. 8 is a conceptual diagram of a dual chamber cardiac pacemaker system 500 in accordance with the instant invention implanted in a body cavity within a patient for which pacing therapy is intended. The system comprises a biological lithium/oxygen semi-fuel cell 110, as described above, electrically coupled, via power cell leads 130, to pacemaker device 120.

In use the stimulating electrodes (501, 502) may be implanted in the ventricle of the heart and/or in the atrium (e.g., a first stimulating electrode in the right ventricle (lower chamber) and a second stimulating electrode in the right atrium (upper chamber)). The power cell may be implanted outside the rib cage but under the skin or alternatively in a pocket created under the skin in the abdomen or in a pocket created in the upper chest under the skin or other suitable cavity.

The cardiac pacemaker system of the instant invention has a number of advantages when compared to conventional pacemaker devices, including device longevity given that the oxygen supply is a fuel provided by the body itself and that the anode assembly in losing internal mass during discharge, as opposed to generating internal mass, does not suffer from the same progressive impedance rise as do many other pacemaker batteries, such as Li/I. Moreover, the ability to simply change out the anode assembly, as needed, or when the lithium is exhausted, provides another mechanism to increase device longevity beyond that achievable with conventional pacemakers where closed, or self contained, battery constructions are employed and the whole battery must be changed out at once.

Furthermore, depending on its use protocol, pacemaker system 500 may be a dual system device having a primary function to provide electrical stimulation to the heart and a secondary function which is to deliver lithium ions for nutritional or otherwise beneficial purpose, e.g., for medicinal use. Dual functionality may be particularly advantageous for the elderly, where lithium deficiency in the diet is common and has been associated with various maladies, including geriatric disorders such as alzheimers and dementia. Indeed, having some lithium in the diet is beneficial. The amount of lithium delivered to the subject may be directly proportional to the current passing from the power cell to the IMD, or where additional lithium is deemed beneficial the IMD may be operated in a mode where lithium is delivered at a rate greater than or at a time other than that which is required for stimulating an electrical impulse to the heart or otherwise needed for providing electrical power to the IMD (e.g., pacemaker main module).

Conclusion

Various embodiments of the invention have been described. However a person of ordinary skill in the art will recognize that various modifications may be made to the described embodiments without departing from the scope of the claims. For example, although described primarily with reference to a cardiac pacemaker IMD, the invention is not so limited. The techniques of this disclosure and the inventive power cell described herein may be embodied in a suitable IMD system as would be recognized by one of skill in the art.

Moreover, although the foregoing invention has been described in some detail with respect to a biological lithium power cell for purposes of clarity of understanding, it will be apparent that certain changes and modifications may be practiced within the scope of the invention. Accordingly, the present embodiments are to be considered as illustrative and not restrictive, and the invention is not to be limited to the details given herein.

Moreover, although the invention has been described in detail with respect to implantable devices (i.e., power cells) for powering implantable medical devices and IMD systems derived therefrom, the invention is not intended to be restricted to medical applications and may include other implantable applications including, but not limited to, telemetry (homing devices) and identification tagging.

What is claimed is:

1. An implantable electrochemical power cell device for providing electrical power to an implantable medical device (IMD), the power cell device comprising:
 a first and a second electrode assembly not enclosed in a common housing, the first and second electrode assemblies adapted for implantation into a human subject;
 wherein,
 the first electrode assembly is a hermetically sealed anode assembly comprising:
  an electroactive component material, the electroactive component material being chemically incompatible in contact with water, the electroactive component material comprising an active metal; and
  a biocompatible water-impermeable housing defining an interior volume in which the electroactive component material is disposed, the biocompatible water-impermeable housing comprising an active wall member having an exterior surface facing an external environment outside the biocompatible water-impermeable housing and an internal surface facing an internal environment inside the biocompatible water-impermeable housing, the active wall member: i) conductive to ions of the active metal, ii) impermeable to water in contact with the exterior surface, and iii) in active metal ion communication with the electroactive component material; and
 the second electrode assembly is a cathode assembly;
 wherein,
 the power cell device is implantable in a human subject such that a bodily fluid of the subject could serve as an electrolytic medium between the first and second electrode assemblies during discharge of the electrochemical power cell device.

2. The implantable electrochemical power cell device of claim 1 wherein the active metal is lithium.

3. The implantable electrochemical power cell device of claim 1 wherein the electroactive component material is lithium metal.

4. The implantable electrochemical power cell device of claim 1 wherein the exterior surface composition of the active wall member is a titanium compound conductive of lithium ions.

5. The implantable electrochemical power cell device of claim 1 wherein the exterior surface composition of the active wall member is a metal phosphate compound conductive of lithium ions.

6. The implantable electrochemical power cell device of claim 1 wherein the exterior surface composition of the active wall member is a lithium titanium phosphate compound conductive of lithium ions.

7. The implantable electrochemical power cell device of claim 1 wherein the anode housing is integrally formed via cooperation of the active wall member and at least one inactive wall member.

8. The implantable electrochemical power cell device of claim 7 wherein the inactive wall member is a receptacle having a unitary structure for receiving said electroactive component material, wherein said receptacle has an open end which is hermetically sealed via cooperation with the active wall member.

9. The implantable electrochemical power cell device of claim 8 wherein the receptacle comprises a titanium capsule.

10. The implantable electrochemical power cell device of claim 1 wherein the inactive wall member further comprises an electrical feedthrough connector configured for electrical coupling to an implantable medical device, the connector electrically coupled to the electroactive component material.

11. The implantable electrochemical power cell device of claim 1, wherein the implantable electrochemical power cell device is a biological semi-fuel cell, wherein the cathode assembly comprises an electron transfer medium for electroreducing a constituent of a bodily fluid in contact with which said transfer medium is adapted to be placed.

12. The implantable electrochemical power cell device of claim 11 wherein the constituent is dissolved oxygen.

13. The implantable electrochemical power cell device of claim 11 wherein the cathode assembly further comprises a biocompatible sheath covering a backside, edges and corners of the electron transfer medium.

14. The implantable electrochemical power cell device of claim 13 wherein the biocompatible sheath comprises an electrical feedthrough connector configured for electrical coupling to an implantable medical device, the connector electrically coupled to the electron transfer medium.

15. The implantable electrochemical power cell device of claim 14 further comprising a first lead electrically coupled to the electroactive component material and a second lead electrically coupled to the electron transfer medium;
 whereby said leads serve to provide passage of electrons between their respective electrode assemblies and an IMD.

16. The implantable electrochemical power cell device of claim 15 wherein at least one of the first lead or second lead is configured for detachable coupling to either the IMD or its respective electrode assembly, first or second.

17. The implantable electrochemical power cell device of claim 15 wherein at least one of the first lead or second lead is configured for detachable coupling to both the IMD and its respective electrode assembly.

18. The implantable electrochemical power cell device of claim 1 wherein the biocompatible water-impermeable housing further comprises an active metal ion conducting interlayer interposed between the active wall member and the electroactive component material, the interlayer in contact with the active wall member interior surface and the electroactive component material.

19. The implantable electrochemical power cell device of claim 18 wherein the active metal ion conducting interlayer comprises an electrolyte selected from the group consisting of liquid, gel and solid phase lithium ion conductors chemically compatible in contact with the electroactive component material.

20. The implantable electrochemical power cell device of claim 1 wherein the implantable electrochemical power cell device has an integrated configuration, the first assembly attached to the second assembly.

21. The implantable electrochemical power cell device of claim 1 wherein the first and second electrode assembly are not attached, and at least one of the first electrode assembly or second electrode assembly is electrically and mechanically tethered to the IMD via an electrical lead wire.

22. The implantable electrochemical power cell device of claim 21 wherein the first and second electrode assembly are not attached, but rather each is independently electrically and mechanically tethered to the IMD via a first and a second electrical lead wire, respectively.

23. An implantable medical device system comprising:
an implantable device for use implanted in a mammalian subject; and
an implantable electrochemical power cell device for providing electrical power to said device, wherein;
the power cell device comprises a first and a second electrode assembly not enclosed in a common housing, the first and second electrode assemblies adapted for implantation into a human subject; and further wherein,
the first electrode assembly is a hermetically sealed anode assembly comprising:
an electroactive component material, the electroactive component material being chemically incompatible in contact with water, the electroactive component material comprising an active metal; and
a biocompatible bodily fluid water-impermeable housing defining an interior volume in which the electroactive component material is disposed, the biocompatible water-impermeable housing comprising an active wall member having an exterior surface facing the an external environment outside the biocompatible water-impermeable housing and an internal surface facing the an internal environment inside the biocompatible water-impermeable housing, the active wall member: i) conductive to ions of the active metal, ii) impermeable to ambient air and water in contact with the exterior surface, and iii) in active metal ion communication with the electroactive component material; and
the second electrode assembly is a cathode assembly; wherein,
the power cell device is implantable into a human subject such that a bodily fluid of the subject can serve as an electrolytic medium between the first and second electrode assemblies during cell discharge.

24. The system of claim 23 wherein the device comprises a secondary energy storage component, and the power cell device provides electrical energy to charge said secondary energy storage component.

25. The system of claim 24 wherein said secondary energy storage component is a battery.

26. The system of claim 25 wherein said battery is a lithium ion secondary battery.

27. The system of claim 24 wherein said secondary energy storage component is a capacitor.

28. The system of claim 23 wherein the system is a cardiac pacemaker.

29. The system of claim 23 wherein the system is adapted to provide a primary function and a secondary function different than the primary function.

30. The system of claim 29 wherein the primary function is the delivery of a stimulating electrical pulse to an organ of the subject in which the device is adapted for implantation.

31. The system of claim 30 wherein the organ is the subject's heart.

32. The system of claim 29 wherein the secondary function is the delivery of said active metal ion for nutritional benefit to the subject in which the power cell device is adapted for implantation.

* * * * *